(12) United States Patent
Chang

(10) Patent No.: US 6,663,562 B2
(45) Date of Patent: Dec. 16, 2003

(54) SURGICAL RETRACTOR

(76) Inventor: David Chang, 545 Pierce St., #2305, Albany, CA (US) 94706

( * ) Notice: Subject to any disclaimer, the term of this patent is extended or adjusted under 35 U.S.C. 154(b) by 0 days.

(21) Appl. No.: 09/953,093

(22) Filed: Sep. 14, 2001

(65) Prior Publication Data

US 2003/0055319 A1 Mar. 20, 2003

(51) Int. Cl.⁷ .................................................. A61B 17/00
(52) U.S. Cl. ...................................... 600/219; 600/213
(58) Field of Search ................................. 600/201, 210, 600/218, 219, 222, 225, 213; 606/205, 207

(56) References Cited

U.S. PATENT DOCUMENTS

| | | | |
|---|---|---|---|
| 569,839 A | * 10/1896 | Roeloffs | ...................... 600/213 |
| 1,018,868 A | 2/1912 | Breneman | |
| 1,500,227 A | 7/1924 | Breneman | |
| 1,727,879 A | * 9/1929 | Hodlick et al. | ............. 600/219 |
| 4,747,395 A | 5/1988 | Brief | |
| 5,728,046 A | 3/1998 | Mayer et al. | |
| 5,931,777 A | 8/1999 | Sava | |
| 5,993,385 A | * 11/1999 | Johnston et al. | ............. 600/213 |
| 6,196,969 B1 | * 3/2001 | Bester et al. | ............... 600/224 |
| 6,261,296 B1 | * 7/2001 | Aebi et al. | ..................... 606/90 |

* cited by examiner

Primary Examiner—Cary E. O'Connor
(74) Attorney, Agent, or Firm—Brian Beverly

(57) ABSTRACT

A surgical retractor comprises a pair of arms having a common pivotal connection and a pair of retractor blades, each blade detachably connected to an arm by a rotating knee joint which allows the retractor blade to rotate about an axis parallel to the arm and also about an axis perpendicular to the arm. A detent locking mechanism allows any selected pair of a plurality of pairs of retractor blades to be detachably attached to the arms. The knee joint comprises an open sleeve for easy sanitizing. The arms are opened and closed using handles having a locking ratchet mechanism and pawl allowing the arms to be locked in any open position.

18 Claims, 5 Drawing Sheets

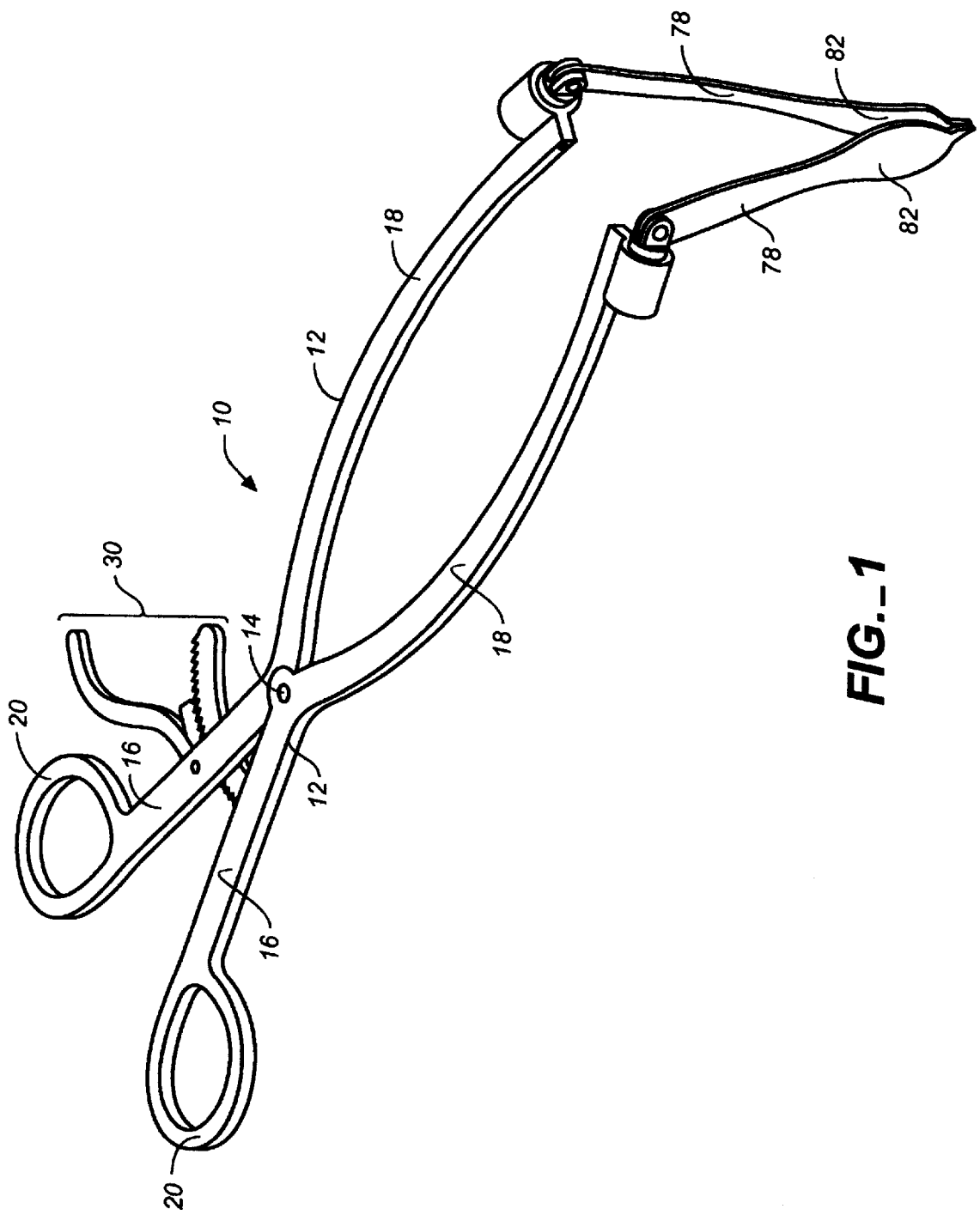
FIG._1

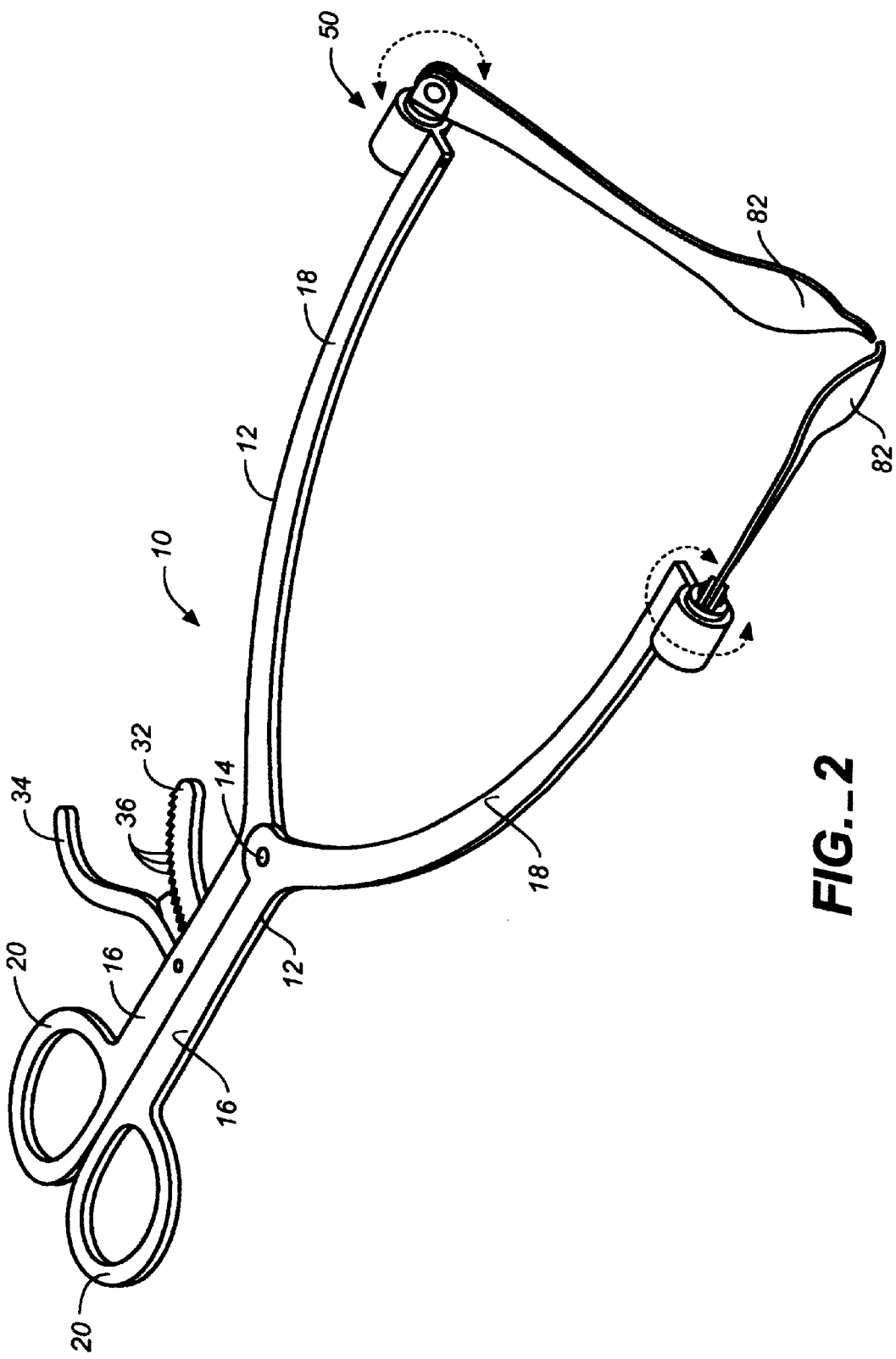
FIG._2

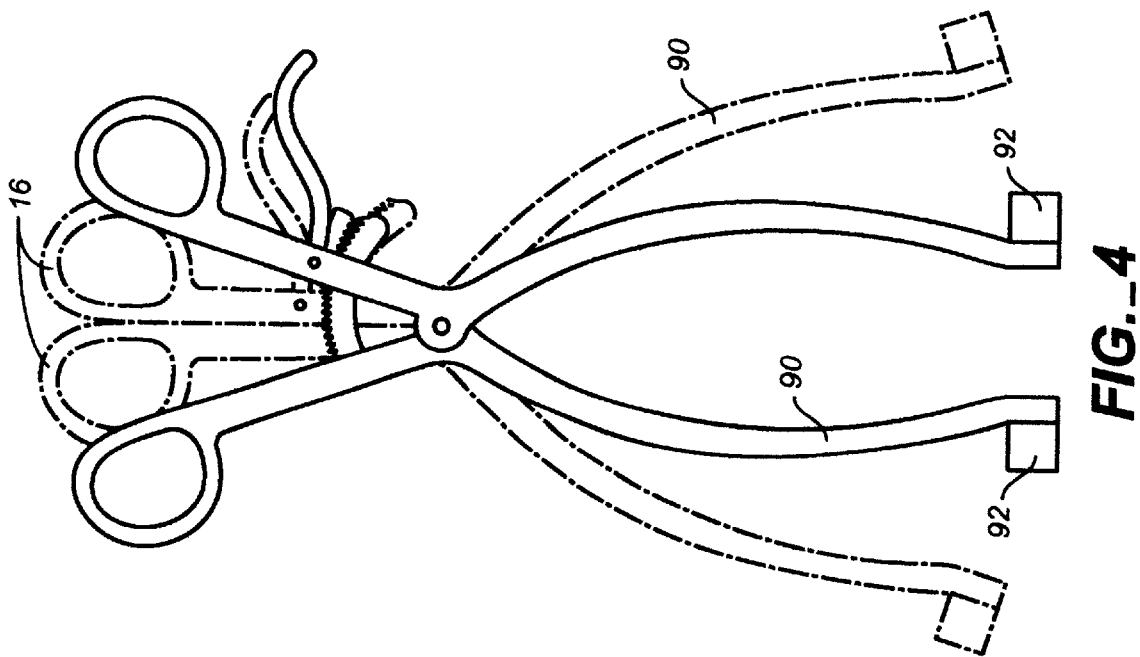
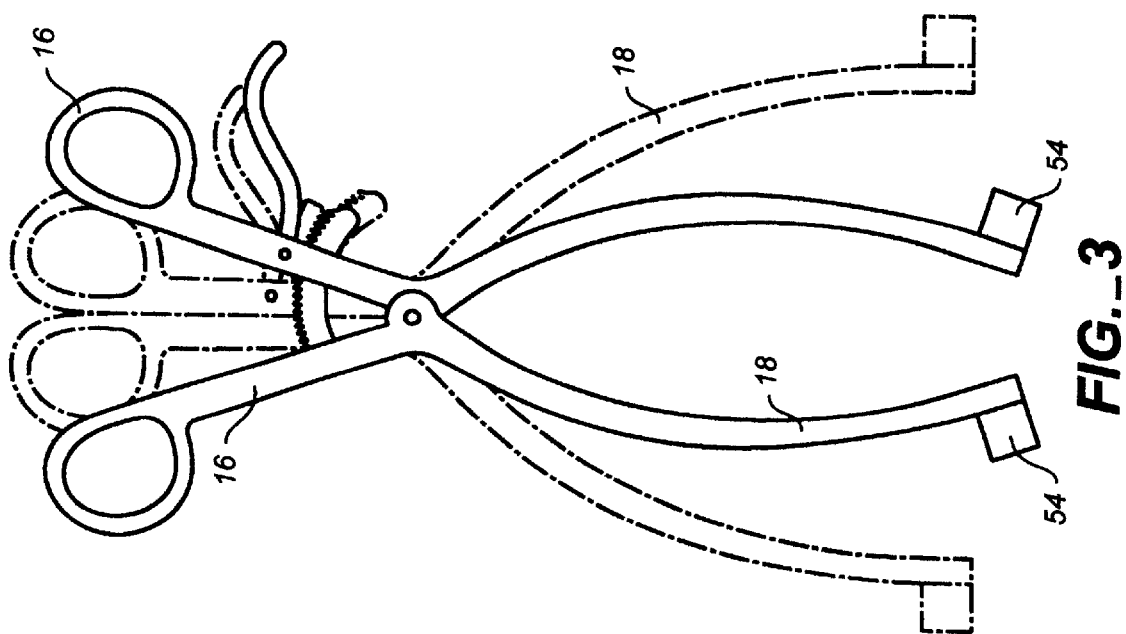

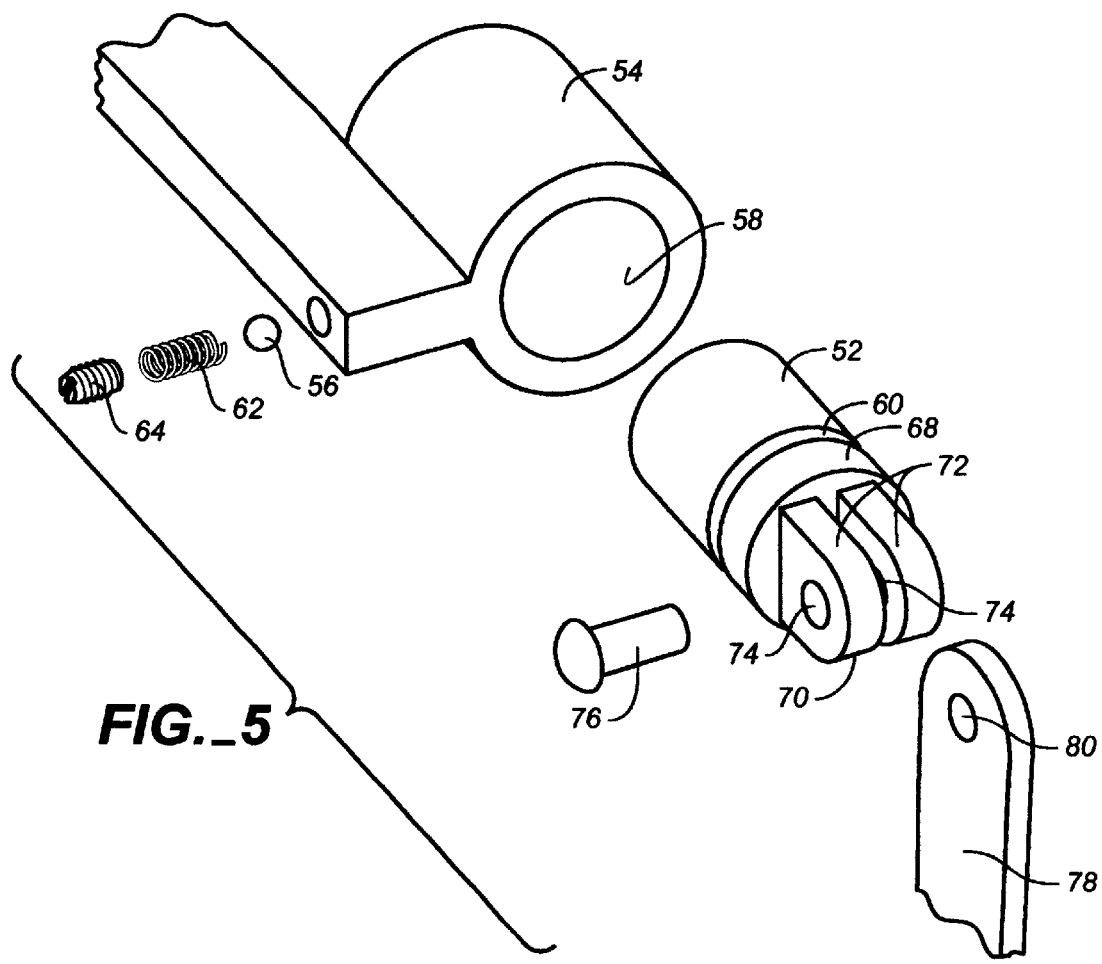
*FIG._5*
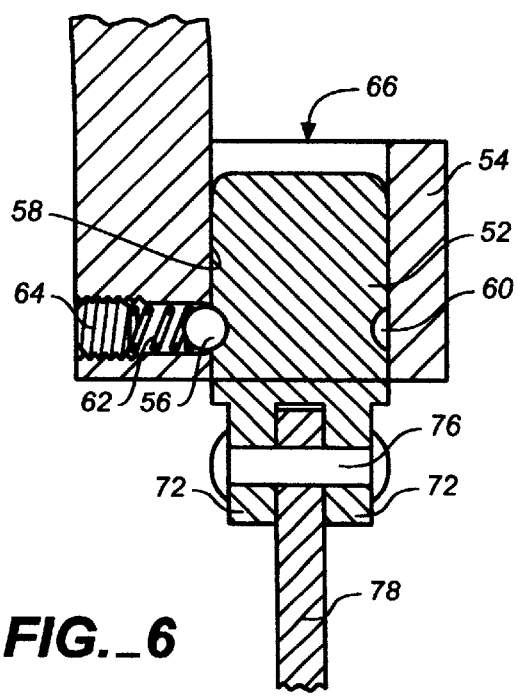
*FIG._6*

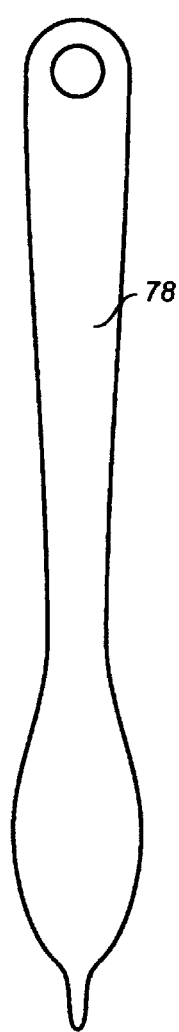
FIG. 7A  FIG. 7B
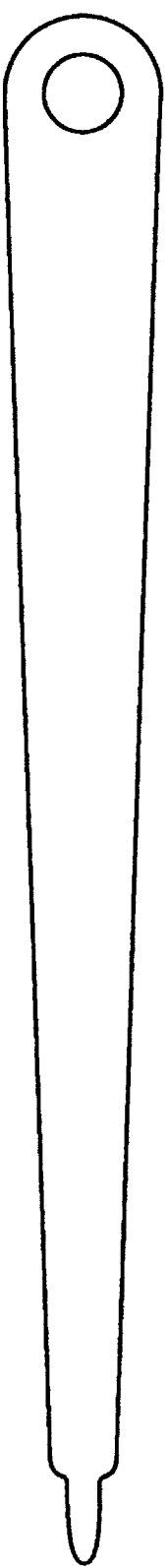
FIG. 8A  FIG. 8B

SURGICAL RETRACTOR

BACKGROUND OF THE INVENTION

This invention relates to surgical retractors, and more particularly pertains to a new and improved surgical retractor of the bone retracting type.

In commencing a surgical procedure, an orthopaedic surgeon makes one or more incisions in a human body. In order to obtain unhindered access to underlying long bones, the surgeon then uses a retractor to dilate or reflect the skin and underlying layers of tissue. The purpose of retractors is to protect soft tissue around a bone and to allow visualization of a wound including the bone. A typical retractor is formed from surgical steel and includes one or more smooth projections, generally termed "blades," which retain an area of tissue adjacent to an incision. The retracting blades can be designed with a blunt or pointed distal projection which engage and pivot around a long bone, thus dilating skin and tissue thereby providing access to the bone. A simple retractor may include only a blade attached to a handle. A blade may vary in length and width, and the surface of a blade may be described as being either closed-end (solid) or open-end (open within the periphery). A blade may be straight or curved.

Use of a conventional retractor requires the surgeon to use one hand to operate the retractor, leaving only the other hand to perform functions such as positioning additional retractor blades, otherwise improving exposure, or surgical operations. Frequently a surgical assistant is required to manipulate the retractors to maintain adequate exposure while the surgeon performs the bone work.

Members of the surgical staff who use a hand-held retractor during procedures in which the duration of the case is relatively long and the forces exerted by the tissue upon the retractor are relatively large, may suffer from fatigue and be subject to injury resulting from the necessity of constantly applying pressure to maintain tissue retraction. It is therefore desirable to provide a tissue retractor that allows controlled retraction against relatively high resistance of tissue during lengthy surgical sessions.

Members of the surgical staff who will be using a conventional bone retractor are also subjected to the risks of injury from sharp instruments passed between the incision and the back table. Violation of the sterile field as such exposes the assistant to potential blood-borne infection and exposes the patient to blood-borne, bacterial and fungal infections.

Additionally, different surgical approaches or bone exposures demand distinct visualizations depending on variables such as wound depth, wound length, soft tissue tension, long bone size, and surgical illumination. It is therefore desirable to facilitate use of retractor blades of differing dimensions to accommodate the specific procedure contemplated.

It is important that a retractor efficiently transmit force exerted by the user's hand to the blades. Limitations on conventional hand-held dilating retractors lead many surgeons to reject their use during certain procedures.

Several salutary efforts have been made to provide improved tissue retractors. U.S. Pat. No. 5,931,777 to Sava, for example, discloses a tissue retractor for particular application to spinal surgery comprising a pair of pivotally linked arms, each having a retractor blade mounted thereto via a ball and socket joint. The ball and socket joint allows freedom of movement relative to the arms within the limits of the ball joint. The balls and sockets of each joint are detachable from each other for cleaning and sterilization. Pilot holes are drilled in bone at a distance defining a surgical field. Piercing tips at the base of each blade are inserted into the pilot holes, anchoring the blades in place. A supplemental retractor blade or blades may be provided using a U-shaped linking structure for additional retraction perpendicular to the retraction provided by the main retractor blades. One disadvantage of the Sava device is that the arms may expand only within the limits of the ball joint, expansion beyond which may cause the ball to pop out of the socket. The possible degree of exposure is therefore limited. A second disadvantage is that the piercing tips on the retractor blades are inappropriate for long bone surgery. Third, although the blades are detachable, the ball and socket joint is not ideal for convenient exchange of a selection of modular blades appropriate for different requirements Fourth, the drilling of pilot holes in bone is undesirable because it is time consuming and creates stress risers in bone which can predispose the bone to fracture. Thus, the Sava retractor is of limited efficiency, may experience metal fatigue at the locus of the expansion joint, and may fail at its limits of expansion.

U.S. Pat. No. 4,747,395 to Brief discloses a surgical retractor for large bone surgery, particularly femur surgery, comprising a pair of retractor members each having an upper lever arm section. The upper lever arm sections receive a U-shaped expander for expanding and locking in place the upper sections of the lever arms. The utility of the Brief retractor is limited because two or more hands are required to manipulate it. Another disadvantage is that movement of the retractor blades is restricted to one plane, which may result in alignment problems. Further, the configuration of the blades is not conducive to modular blade selection and its large size does not allow its use in surgery involving smaller bones.

U.S. Pat. No. 5,728,046 to Mayer discloses a surgical retractor having a frame on which at least two retractor elements are mounted. The frame is rigidly mounted to a bone with at least one support foot, thus allowing retractor blades to be positioned on individual tissue parts bearing different pressing forces. The Mayer device is complicated and must be screw-anchored in bone. The device's configuration and retractor blades are not suited to long bone surgery. Mayer also requires both hands to operate. As with Sava, above, the device penetrates bone in order to work properly, compromising the healing process, and predisposing the bone to fracture.

SUMMARY OF THE INVENTION

An improved surgical retractor for use in long-bone surgery comprises a pair of arms and a retractor blade connected to each arm by a detachable, rotating knee joint which facilitates adjustment and alignment of the blade in dual planes of movement. In particular, each arm has a handle and a distal portion. The arms have a common pivotal connection disposed between the handle and distal portions of each arm. Since each arm is angled outwardly from the pivotal connection, closing the handles causes the arms to mutually recede.

Immediately adjacent the handles, a curved locking ratchet mechanism and thumb-operated pawl control the distance of separation of the arms and allow them to be locked at any selected degree of separation.

A knee joint having a detent locking mechanism is used to affix a long-bone retractor blade to the distal portion of each arm. The detent locking mechanism allows any selected pair of retractor blades to be attached to the arms. Once mounted to the arm, each retractor blade is rotatable about an axis parallel to the arm and also about an axis perpendicular to the arm. These plural aspects of rotation allow the surgeon substantial freedom in positioning the blades and the handles once the blades are in their retracted positions.

The invention uses bone retractor blades of the type having a remote, curved, long bone-engaging tongue. Using long bone retractor blades eliminates the need for a piercing tip in the blade and for drilling a pilot hole in the bone to anchor the retractor. When each of the two retractor blades is placed in position on a long bone, closing the handles causes the retractor blades to recede from each other, pivoting around the bone, and opening the angle of the wound, effectively retracting surrounding tissue from the bone.

A distinct advantage of using the improved retractor is that a surgeon need use only one hand to position and open the retractor, freeing the other hand to perform other functions such as positioning the blades or otherwise improving exposure. Once the retractor is locked in place, both hands are free to perform other surgical procedures. This convenience may allow a procedure to be performed using a smaller surgical staff, thereby minimizing the number of surgical tools required, reducing the risks of injury to surgical personnel, reducing labor costs, and lowering the potential for infections to the patient and surgical staff from violations of the sterile field. Further, applicant's retractor allows endless controlled tissue retraction against a relatively high resistance of tissue as the pawl and ratchet are engaged.

Another advantage of using applicant's improved retractor is that it exposes the bone and allows superior visualization of the site without interference from the assistant surgeon's hand, which otherwise may obstruct the surgeon's view or block light from overhead surgical lamps, especially into a deep wound.

The present invention provides a hand-held surgical retractor having a pair of retractor blades which transmit force from the hand to the blades with efficiency. This device is useful in procedures involving deep wounds, such as those involving long bones in which it may formerly have been thought suitable to use only hand-held dilating retractors.

It is another object of the invention to provide a tissue retractor having self-aligning and self-retaining properties such that, after the retractor blades are engaged on a bone and the handle deployed, visualization of the surgical field is achieved without the need for hands-on manipulation of the retractor.

During a surgical procedure, the surgeon or an assistant places the retractor on the surface of the body of the patient and inserts two blades within the opening created by a body cavity, an incision, or wound. The blades are then engaged onto the handle via the knee joint. The handles are closed, opening a space between the two blades as the blades draw apart from each other. A conventional pawl and rachet self-retaining device may then be engaged, and the retractor is left to be supported on the body of the patient during the surgical procedure. At the conclusion of the procedure, the thumb is used to disengage the pawl from the rachet to reopen the handles, thus bringing the blades back together and allowing the wound to close.

In a second embodiment of a retractor according to the invention, the dimensions of one blade may differ from the dimensions of another blade, to accommodate differing visualization and exposure requirements according to the surgical procedure contemplated.

The improved retractor provides for detachment and attachment of any selected pair of retractor blades, facilitating effective retraction under widely varying conditions demanding different degrees of retraction and visualization.

It is therefore a primary object of the invention to provide an improved tissue retractor for single-handed operation of a tissue retractor during a long bone surgical procedure.

It is another object of the invention to provide an improved tissue retractor having a pair of retractor blades detachably mounted on pivotally conjoined arms using swivelling knee joints allowing for freedom of positioning of the retractor during a surgical procedure for improved visualization.

It is a further object of the invention to provide an improved surgical tissue retractor having a pair of retractor blades detachably mounted on pivotally conjoined arms using swivelling knee joints wherein the separation of the arms is controlled by a locking ratchet and pawl mechanism.

It is a yet another object of the invention to provide an improved surgical tissue retractor wherein any pair of a plurality of pairs of retractor blades is selectively attached to pivotally conjoined arms using a detent locking mechanism.

A still further object of the invention is to provide an improved surgical tissue retractor operable without the need of a surgical assistant.

Another object of the invention is to provide a surgical tissue retractor which reduces fatigue and risk of injury to surgeons and surgical staff members who might otherwise be directed to use conventional tissue retractors.

It is a separate object of the invention to provide an improved surgical tissue retractor which is inexpensive to manufacture and easy to manipulate with one hand.

BRIEF DESCRIPTION OF THE DRAWINGS

FIG. 1 is a perspective view of a surgical retractor according to the invention.

FIG. 2 is a perspective view of the surgical retractor of FIG. 1 showing the arms of the retractor in fully open position.

FIG. 3 is a plan view of the levers of the surgical retractor of FIG. 1 shown in a closed position and, in dotted lines, in an open position.

FIG. 4 is a plan view of an alternate embodiment of the surgical retractor of FIG. 1 shown in closed position and, in dotted lines, in open position.

FIG. 5 is a closeup, exploded perspective view of the swiveling knee joint of each arm of the surgical retractor of FIG. 1.

FIG. 6 is a slice view of the swiveling knee joint of FIG. 5 in its fully assembled position.

FIGS. 7A and 7B are a plan view and side view, respectively, of one of the retractor blades shown in FIG. 1.

FIGS. 8A and 8B are a plan view and side view, respectively, of an alternate embodiment of a retractor blade according to the invention.

DETAILED DESCRIPTION OF THE PREFERRED EMBODIMENTS

An improved surgical retractor for use in long bone surgery is illustrated in the accompanying drawings and described below. A surgical retractor 10 according to the invention is shown in FIGS. 1 through 8. With reference to FIG. 1, retractor 10 comprises a pair of levers 12, joined together at a common pivotal connection 14. Each lever comprises a handle 16 and arm portion 18. Preferably, handles 16 include handle loops 20 for more convenient manipulation of the device. Levers 12 are angled outwardly at pivot connection 14 such that, as best seen in FIGS. 3 and 4, when handles 16 are closed, arm portions 18 open.

With reference again to FIG. 1, a locking rachet mechanism 30 is provided to prevent handles 16 in any closed position from unwanted or untimely reopening. Referring to FIG. 2, a locking rachet mechanism preferably comprises a conventional rachet 32 and spring-loaded pawl 34. As handles 16 are closed, pawl 34 slides across teeth 36 of rachet 32. A spring (not illustrated) holds pawl 34 against rachet teeth 36 such that any reversal of movement is prevented by teeth 36 catching in pawl 34. Pawl 34 is mounted to handle 16 at pawl pivot 38, allowing pawl 34 to be pulled away from rachet 32, thereby allowing handles 16 to open and, hence, arms 18 to close.

At a distal end of each arm portion 18 of levers 12 is provided a swiveling knee joint 50. Referring to FIG. 5, the knee joint comprises a cylindrical insert 52 for insertion into sleeve 54. An inwardly spring-biased bearing member 56 is disposed on an inside surface 58 of sleeve 54. An annular channel 60 is provided on cylindrical insert 52, such that when cylindrical insert 52 is inserted into sleeve 54, bearing member 56 snaps into annular channel 60, holding insert 52 in place, but allowing it to rotate freely in sleeve 54 about a longitudinal axis thereof. See FIGS. 1 and 6. Preferably, bearing member 56 comprises a ball bearing, but any component part having a convex head could be used, such as a pin of suitable size. Bearing member 56 is inwardly biased by spring 62 which, in turn, is held in place by set screw 64. Preferably, bearing member 56, spring 62, and set screw 64 are disposed in distal end of arm portion 18, as shown in FIGS. 5 and 6, making effective use of the arm for positioning of those parts to inwardly bias bearing member 56 and eliminating undesirable protrusions which might otherwise interfere with the surgical procedure. However, other means of biasing a bearing member inwardly or placement of spring 62 and set screw 64 are well known in the art. Alternatively, cylindrical insert 52 may have one or more outwardly biased bearing members for snapping into an annular channel on the inside surface of sleeve 54; merely a reverse of the preferred configuration. As seen in FIG. 6, sleeve 54 is open not only at its front end, wherein the cylindrical insert is introduced, but also is open at a back end 66. Sleeve 54 thereby has a central through-bore open on both ends, greatly facilitating thorough cleaning and sanitizing of the knee joint, as is highly desirable in a surgical setting. If desired, screw 64, spring 62, and bearing member 56 may easily be removed for cleaning and sanitizing purposes.

Referring back to FIG. 5, attached to a base portion 68 of insert 52 is provided pivot joint 70. Pivot joint 70 comprises dual hinge plates 72 having common aligned apertures 74 for insertion therein of pivot pin 76. A retractor blade 78 is provided with hole 80, having approximately the same diameter as apertures 74. Retractor blade 78 is pivotally attached to cylindrical insert 52 by insertion of pivot pin 76 through apertures 74 in hinge plates 72 and through hole 80 in retractor blade 78, as seen in FIG. 6. When cylindrical insert 52 is resident in sleeve 54, pivot pin 76 defines a pivot axis perpendicular to the longitudinal axis of sleeve 54. See FIGS. 2 and 5.

In a surgical theater, a pair of retractor blades selected according to the surgical requirements of the case are quickly snapped into place in sleeves 54, as shown in FIG. 1. The device is then positioned over the wound and, with handles open—arms closed, bone-engaging portions 82 are circumferentially positioned around a long bone. Closing of handles 16 opens arm portions 18, as shown in FIG. 3. This in turn spreads retractor blades 78 as shown in FIG. 2, thereby retracting tissues surrounding the long bone and providing improved visibility of the surgical site with minimal effort. Each retractor blade has a concave inner face for engaging the bone. Accordingly, opening arms 18 against the inward pressure of wound-surrounding soft tissue forces the bone-engaging portions of opposing retractor blades 82 against the bone. Blades 82 therefore self-align on the bone and can be maintained in position without the need for bone-piercing end points. Locking rachet mechanism 30 retains the retractor blades in place without need for the surgeon or surgical assistant to hold them in position. The surgical retractor thus reduces the number of hands needed for the operation, opens the wound for improved visibility and surgical access with reduced effort, and minimizes the fatigue associated with prior art methods of retracting tissue around a wound. The invention requires little, if any, lubricant, thereby removing or substantially reducing a contamination issue.

The overall simplicity and efficiency of a surgical retractor according to the invention will allow it to be considered for operations previously thought unsuitable for the use of hand-held retractors.

It is recommended that the surgical retractor be constructed of surgical steel or other strong, light, highly polished metal. The exact dimensions of levers 12 and retractor blades 78 depend upon the surgical procedure to be performed and the relative positions of the retractor blades which may be desirable depending upon the nature of the surgical case. FIG. 8 shows an alternative embodiment of a pair of retractor blades which may be better suited for a deeper wound than the retractor blades illustrated in FIGS. 7A and 7B.

FIG. 4 shows an alternate embodiment of arms to that shown in FIG. 3. As seen in FIG. 4, when arms 90 are in closed position, sleeves 92 are in parallel relation, whereas arms 18 in the embodiment illustrated in FIG. 3 must be in open position for sleeves 54 to be in parallel relation. The choice of either embodiment is a matter of preference for the surgeon, depending on the surgeon's view of whether the retractor blades will be in better position at varying points in the surgical procedure with one embodiment as opposed to another. More particularly, using the embodiment shown in FIG. 3, the retractor blades will be in parallel opposing relation engaged on the long bone when arms 18 are in fully open position, but will be at a small angle to each other when arms 18 are in their closed position. The reverse is true when the embodiment shown in FIG. 4 is used.

There have been discussed and illustrated certain preferred embodiments of a surgical retractor, according to the invention. Although the present invention has been described and illustrated in detail, it is clearly that the same is by way of illustration and example only and is not to be taken by way of limitation, the spirit and scope of the present invention being limited only by the terms of the appended claims and their legal equivalents.

I claim:

1. A tissue retractor for surgery comprising:
   a pair of levers having a common pivotal connection, said pivotal connection disposed between a handle and an arm portion of each lever, said levers each angled outwardly from said pivotal connection for drawing apart the arm portions thereof by closing said handles, and a pair of swivelling knee joints each coupling a proximal portion of one of a pair of retractor blades with the arm portion of one of said levers, each retractor blade having a concave face, said concave faces of said retractor blades in facing relation for simultaneous sliding circumferential engagement with an outer surface of a long bone.

2. A tissue retractor for bone surgery comprising:

a pair of levers having a common pivotal connection, said pivotal connection disposed between a handle and an arm portion of each lever, said levers each angled outwardly from said pivotal connection for drawing apart the arm portions thereof by closing said handles, each arm portion having a swivelling knee joint, each said swivelling knee joint including a sleeve, a cylindrical insert for detachable insertion into said sleeve, and a pivot joint, said cylindrical insert freely rotatable about a longitudinal axis of said sleeve, said pivot joint integrally attached to said cylindrical insert, and a pair of retractor blades each having a proximal portion, said pivot joint of said swivelling knee joint pivotally coupling said proximal portion of one of said retractor blades to said cylindrical insert, such that said retractor blade pivots about an axis perpendicular to said longitudinal axis of said sleeve.

3. The tissue retractor of claim 2 wherein:

said sleeve is integral with the arm of said lever.

4. The tissue retractor of claim 2 wherein:

said pivot joint further comprises a pivot pin, said pivot pin disposed perpendicularly to said longitudinal axis of said sleeve, and said retractor blade pivots about said pivot pin.

5. The tissue retractor of claim 2 wherein:

said pivot joint permits limited twisting movement of said retractor blade about a longitudinal dimension of said retractor blade such that a concave blunted tongue of the bone engaging portion of said retractor blade remains engaged with an outer surface of a long bone at all degrees of separation of the arms of said levers.

6. The tissue retractor of claim 2 wherein:

said arms each have a distal end, each said sleeve defines a central bore, and said central bore of each said sleeve is parallel with said distal end of one of said arms.

7. A tissue retractor for bone surgery comprising:

a pair of levers having a common pivotal connection, said pivotal connection disposed between a handle and an arm portion of each lever, said levers each angled outwardly from said pivotal connection for drawing apart the arm portions thereof by closing said handles, said arms each having a distal end, and a pair of swivelling knee joints, each said swivelling knee joint including a sleeve having a bore in parallel relation with said distal end of one of said arms, each said swivelling knee joint also including a cylindrical insert for detachable insertion into said bore of said sleeve, each said swivelling knee joint coupling a proximal portion of one of a pair of retractor blades with said arm portion of one of said levers.

8. The tissue retractor of claim 7 further comprising:

a plurality of pairs of retractor blades, wherein said retractor blades are detachable from the arms of said levers for attachment of any selected pair of said plurality of pairs of retractor blades to said arms according to applicable surgical requirements.

9. The tissue retractor of claim 7 wherein:

said swivelling knee joint further comprises a detent locking mechanism for detachably retaining said cylindrical insert in said sleeve, said cylindrical insert freely rotatable about a longitudinal axis of said sleeve.

10. The tissue retractor of claim 9 wherein:

said detent locking mechanism comprises said cylindrical insert having a circumferential channel on an outside face thereof for engagement with at least one inwardly biased pin on an inside face of said sleeve.

11. The tissue retractor of claim 10 wherein:

said detent locking mechanism further comprises a spring for biasing said pin and a set screw for holding said spring against said pin.

12. The tissue retractor of claim 7 wherein:

said sleeve further comprises a central through bore for insertion therein of said cylindrical insert, said sleeve open on a front end at said bore and on a back end at said bore for ease of cleaning.

13. The tissue retractor of claim 7 wherein:

said cylindrical insert is freely rotatable about a longitudinal axis of said sleeve.

14. The tissue retractor of claim 7 wherein:

when said arms are at a maximum separation, said sleeves are in approximately parallel relation.

15. A tissue retractor for bone surgery comprising:

a pair of levers having a common pivotal connection, said pivotal connection disposed between a handle and an arm of each lever, said levers each angled outwardly from said pivotal connection for drawing apart the arms thereof by closing said handles, the arm of each lever having an integral sleeve, said sleeve parallel with a distal end of said arm, a pair of swivelling knee joints, each said knee joint having a cylindrical insert detachably inserted into one of said sleeves and rotatable about a longitudinal axis thereof, each knee joint further having a pivot joint integrally attached to a base portion of said insert, and a proximal portion of each of a pair of retractor blades pivotally connected to one of said inserts at said pivot joint, said retractor blade depending from said pivot joint for pivoting movement about a pivot axis disposed perpendicularly to said sleeve.

16. The tissue retractor of claim 15 wherein:

said pivot joint comprises a pivot pin.

17. The tissue retractor of claim 16 wherein:

said pivot joint permits limited twisting movement of said retractor blade about a longitudinal dimension of said retractor blade such that a bone engaging portion of said retractor blade remains engaged with an outer surface of a long bone at all degrees of separation of the arms of said levers.

18. A tissue retractor for bone surgery comprising:

a pair of levers having a common pivotal connection, said pivotal connection disposed between a handle and an arm portion of each lever, a locking ratchet mechanism for locking said arm portions in a selected separated relationship, said levers each angled outwardly from said pivotal connection for drawing apart the arm portions thereof by closing said handles, and a pair of swivelling knee joints each coupling a proximal portion of one of a pair of retractor blades with the arm portion of one of said levers, each said swivelling knee joint including a sleeve, each said sleeve integrally attached to a distal portion of the arm portion of one of said levers, a cylindrical insert for insertion into said sleeve, a detent locking mechanism for detachably retaining said cylindrical insert in said sleeve, said cylindrical insert freely rotatable in said sleeve about a longitudinal axis of said sleeve, a pivot joint integrally attached to a base of said cylindrical insert, said retractor blade pivotally coupled to said cylindrical insert at said pivot joint, such that said retractor blade pivots about an axis perpendicular to said longitudinal axis of said sleeve, each retractor blade having a bone engaging portion for sliding circumferential engagement with an outer surface of a long bone.

* * * * *